United States Patent
Yang et al.

(10) Patent No.: US 11,958,820 B2
(45) Date of Patent: Apr. 16, 2024

(54) METHOD FOR PURIFYING ETHYLENE CARBONATE THROUGH DYNAMIC CRYSTALLIZATION

(71) Applicant: SHENZHEN CAPCHEM TECHNOLOGY CO., LTD., Shenzhen (CN)

(72) Inventors: Baichun Yang, Shenzhen (CN); Qiyou Huang, Shenzhen (CN); Zihao Ye, Shenzhen (CN); Ao He, Shenzhen (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/081,715

(22) Filed: Dec. 15, 2022

(65) Prior Publication Data

US 2023/0174499 A1 Jun. 8, 2023

Related U.S. Application Data

(63) Continuation of application No. PCT/CN2022/123772, filed on Oct. 8, 2022.

(30) Foreign Application Priority Data

Oct. 18, 2021 (CN) ............................ 202111211876.7

(51) Int. Cl.
*C07D 317/38* (2006.01)

(52) U.S. Cl.
CPC ................................. *C07D 317/38* (2013.01)

(58) Field of Classification Search
CPC .................................................. C07D 317/38
See application file for complete search history.

(56) References Cited

U.S. PATENT DOCUMENTS 5,355,590 A * 10/1994 Slangen ................. F26B 17/18
34/443

FOREIGN PATENT DOCUMENTS

| CN | 102120609 A | 7/2011 | | |
|----|-------------|--------|---|---|
| CN | 102167304 A | 8/2011 | | |
| CN | 201981022 U | 9/2011 | | |
| CN | 102701909 A | 10/2012 | | |
| CN | 105541758 A | 5/2016 | | |
| CN | 105664521 A | 6/2016 | | |
| CN | 106631800 A | 5/2017 | | |
| CN | 106632224 A | 5/2017 | | |
| CN | 106890475 A | 6/2017 | | |
| CN | 107629030 A | 1/2018 | | |
| CN | 107827865 A | 3/2018 | | |
| CN | 207456091 U | 6/2018 | | |
| CN | 108440489 A | 8/2018 | | |
| CN | 108440489 A | * 8/2018 | ........... | B01D 9/0013 |
| CN | 208667148 U | 3/2019 | | |
| CN | 209178273 U | 7/2019 | | |
| CN | 209541347 U | 10/2019 | | |
| CN | 110668517 A | 1/2020 | | |
| CN | 110878078 A | 3/2020 | | |
| CN | 111004203 A | * 4/2020 | ........... | C07D 317/38 |
| CN | 111004203 A | 4/2020 | | |
| CN | 111100003 A | 5/2020 | | |
| CN | 111100100 A | 5/2020 | | |
| CN | 112516616 A | * 3/2021 | | |
| CN | 112704901 A | 4/2021 | | |
| CN | 214286770 U | 9/2021 | | |
| CN | 214570788 U | 11/2021 | | |
| CN | 113979987 A | 1/2022 | | |
| CN | 215891107 U | 2/2022 | | |
| GB | 1319870 A | 6/1973 | | |

OTHER PUBLICATIONS

Technoforce corporate brochure Online: "https://www.technoforce.net/wp-content/uploads/2018/03/Technoforce-Corporate-Brochure-2018.pdf" 2018.*

Jijun Zhang and Dacheng Yang "A Note on Development of Industrial Drying Technology in China" Drying Technology, 30: 320-325 , 2012.*

Kangle Shao:"Design of the rake dryer", Chem Jiangsu, pp. 49-53.

* cited by examiner

*Primary Examiner* — David K O'Dell

(57) ABSTRACT

The present invention relates to the technical field of chemical industry, and in particular to a method for purifying ethylene carbonate through dynamic crystallization, which includes the following steps: adding an ethylene carbonate-containing raw material into a cavity of a crystallization device under a condition of stirring for dynamic crystallization, wherein the crystallization device further includes a jacket attached and circumferentially disposed along the outer wall of the cavity, the jacket is provided with cooling water therein, a temperature of the cooling water is 1-2.5° C. lower than the temperature in the cavity until a granular ethylene carbonate crystal is generated. The present invention using a rake dryer as the crystallization device to realize dynamic crystallization at a certain rotating speed. The technical solution is simple to operate and short in processing cycle, which facilitates improvement in production efficiency and product quality and is suitable for industrial application.

5 Claims, 1 Drawing Sheet

METHOD FOR PURIFYING ETHYLENE CARBONATE THROUGH DYNAMIC CRYSTALLIZATION

TECHNICAL FIELD

The present invention relates to the technical field of chemical industry, and in particular to a method for purifying ethylene carbonate through dynamic crystallization.

BACKGROUND

Ethylene carbonate (EC) is an excellent solvent which can also serve as an intermediate in organic synthesis. It has a boiling point of 238° C., a melting point of 36.4° C. and a flashing point of 160° C. It is decomposed at a small amount when heated to 200° C., and thus it has relatively higher thermal stability. Moreover, ethylene carbonate (EC) has a relatively higher dielectric constant in an electrolyte solution of organic solvent system, and thus it is a commonly used solvent for a lithium-ion electrolyte solution.

Currently, ethylene carbonate is mainly synthesized from ethylene oxide and carbon dioxide under a system with high temperature and catalyst and in the industry. A side reaction accompanying this reaction will produce by-products such as ethylene glycol and diethylene glycol. The side reaction involves hydration, hydrolysis and moisture absorption characteristics of ethylene carbonate, resulting in impurities and moisture contained in the synthesized ethylene carbonate, which will affect the quality of an electrolyte solution of a lithium-ion battery. Therefore, in order to meet the use requirements of the electrolyte solution, it is necessary to purify the synthesized ethylene carbonate.

In the prior art, a commonly used method for purifying ethylene carbonate is rectification. Such an approach has disadvantages such as high energy consumption and a long operation period. For example, in U.S. Pat. No. 3,074,962, it is proposed to use a method of extractive distillation and/or azeotropic distillation to separate EC from ethylene glycol (EG). Apart from the common problems existed in separation and purification of EC in the aforementioned rectification process, this method also introduces a third substance: an extractant or azeotropic agent, which leads to that the separated EC is still of low purity. Currently, there are also approaches for conducting impurity removal and purification of ethylene carbonate, such as a molecular sieve or activated carbon. For example, CN201010598710.0 proposes a method of conducting dehydration and ethylene glycol removal treatment of an EC material with a purity of about 99.9% by employing molecular sieve adsorption, but the molecular sieve is used at a large amount and can also adsorb EC while adsorbing ethylene glycol and water, resulting in the loss of EC and the reduction of yield, and the requirements of operation conditions are demanding and the process is complicated, and the cost is high.

SUMMARY

In order to solve the aforementioned technical problems, the present invention provides a method for purifying ethylene carbonate through dynamic crystallization, which is simple in operation, low in energy consumption, short in production cycle, capable of purifying more materials at one time, and high in purity of a prepared product.

The present invention provides a method for purifying ethylene carbonate through dynamic crystallization, which includes the following steps: adding an ethylene carbonate-containing raw material into a cavity of a crystallization device through a feeding port of the crystallization device under a condition of stirring for dynamic crystallization, wherein the crystallization device further includes a jacket attached to an outer wall of the cavity and circumferentially disposed along the outer wall of the cavity, the jacket is provided with cooling water therein, a water temperature of the cooling water in the jacket is controlled to be 1-2.5° C. lower than the temperature in the cavity until a granular ethylene carbonate crystal is generated.

In some embodiments of the present invention, a temperature of the ethylene carbonate-containing raw material entering the cavity is 40-80° C., a water temperature of the cooling water in the jacket is 25-35° C., and when the temperature in the cavity is decreased to 33° C., the water temperature of the cooling water in the jacket is controlled to be 1-2.5° C. lower than the temperature in the cavity.

In some embodiments of the present invention, the dynamic crystallization includes stirring performed by rotating a plurality of stirring parts disposed on an inner wall of the cavity at a rotating speed of 15-25 r/min.

In some embodiments of the present invention, the water temperature of the cooling water in the jacket is controlled by a setting program.

In some embodiments of the present invention, the crystal formation in the process of crystallization is initiated by adding a seed crystal at a temperature of 28-29° C.

In some embodiments of the present invention, a time for the crystallization is 2-8 h, and the temperature in the cavity during the crystallization is 29-31° C.

In some embodiments of the present invention, the ethylene carbonate-containing raw material is a direct reaction product and/or an ethylene carbonate material with a content greater than or equal to 80% obtained after preliminary purification of a reaction product.

In some embodiments of the present invention, the amount of the ethylene carbonate-containing raw material entering the cavity is no more than two thirds of an inner cavity volume of the cavity.

In some embodiments of the present invention, the crystallized material is introduced into a centrifuge to separate mother liquor from a crystal.

Compared with the prior art, the present invention has the following advantages:

For the method for purifying ethylene carbonate through dynamic crystallization of the present invention, by using the rake dryer as the crystallization device and utilizing a characteristic that the rake dryer can handle a large amount of materials, a temperature difference range between the temperature in the cavity of the rake dryer and the water temperature of the cooling water in the jacket is controlled to realize dynamic crystallization at a certain rotating speed. By adopting the technical solution involved in the present invention, an ethylene carbonate product of high purity and high yield can be obtained, and by utilizing the characteristic that the rake dryer can purify and process more materials at one time, the method is simple to operate, low in energy consumption and short in production cycle, which facilitates improvement in production efficiency and product quality and is suitable for industrial popularization and application.

In the figures: 1: cavity; 2: jacket; 3: feeding port; 4: discharging port; and 5: rake teeth.

DETAILED DESCRIPTION OF EMBODIMENTS

The following clearly and completely describes the technical solutions in the embodiments of the present invention with reference to the embodiments of the present invention. Apparently, the described embodiments are merely a part rather than all of the embodiments of the present invention. All other embodiments obtained by those of ordinary skills in the art based on the embodiments of the present invention without creative efforts shall fall within the claimed scope of the present invention.

Figure 1:
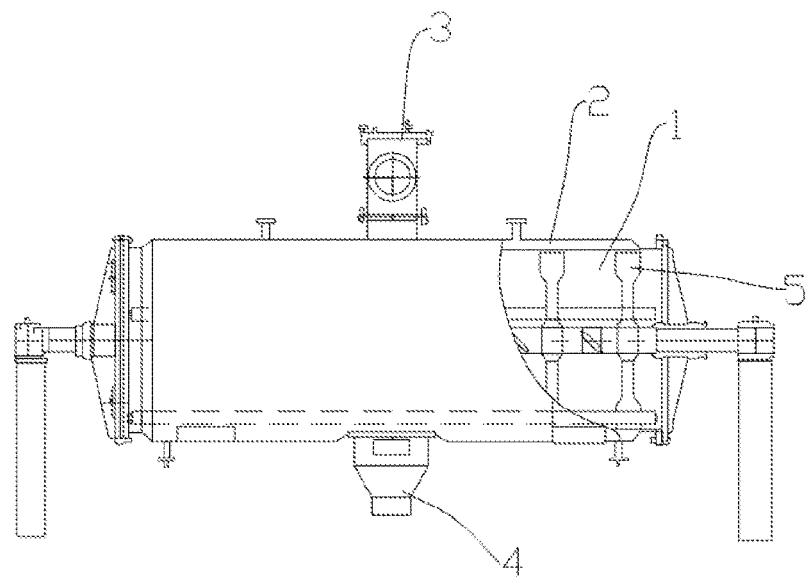
FIG. 1 is a schematic structural diagram of the crystallization device of the present invention.
Figure 2:
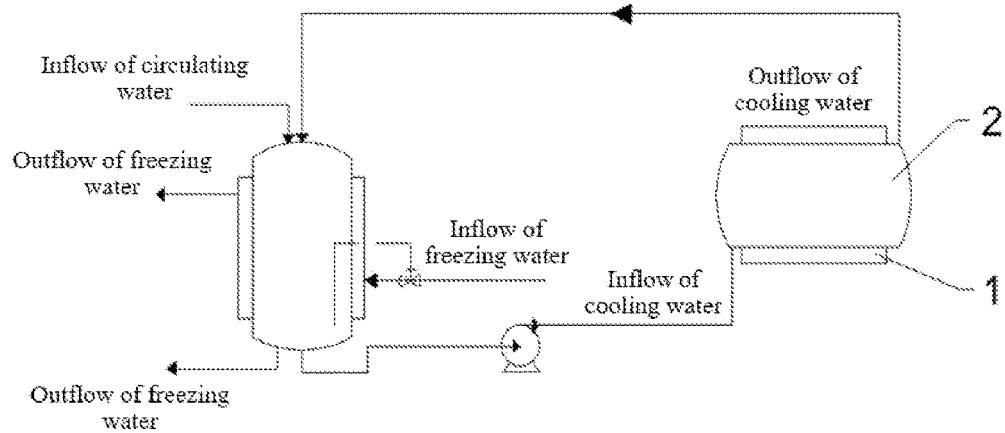
FIG. 2 is a schematic diagram of the circulation of cooling water in the jacket of the present invention.

Referring to FIGS. 1 and 2, a crystallization device includes a cavity 1 for accommodating a crystallization stock solution, and a jacket 2 attached to an outer wall of the cavity 1 and circumferentially disposed along the outer wall of the cavity 1, the jacket 2 is provided with cooling water therein, a feeding port 3 is disposed at a middle position of the top of the cavity 1, a discharging port 4 is disposed on the bottom of the cavity 1 at a position opposite to the feeding port 3, and a plurality of stirring parts arranged at intervals are disposed on an inner wall of the cavity 1.

In the embodiments of the present invention, the crystallization device is a rake dryer, and the cavity 1 for accommodating the crystallization stock solution is disposed in the rake dryer.

In the embodiments of the present invention, the stirring parts are rake teeth 5, and the dynamic crystallization of a material in the cavity 1 is realized by rotating the rake teeth 5 in the cavity 1 according to a certain rotating speed, for example rotating the rake teeth 5 at a rotating speed of 15-25 r/min.

When in use, an ethylene carbonate-containing raw material enters the cavity 1 through the feeding port 3 of the rake dryer for dynamic crystallization. Under the stirring action of the continuously rotating rake teeth 5, the raw material contacts the inner wall of the cavity 1. The jacket 2 is internally connected with circulating cooling water from the outside, and the jacket 2 is attached to the outer wall of the cavity 1, to the temperature in the cavity 1 is gradually reduced by the circulating cooling water connected into the jacket 2 from the outside. The temperature in the kettle is 40-80° C. when the ethylene carbonate-containing raw material enters the cavity 1, the water temperature of the cooling water in the jacket 2 is 25-35° C., and when the temperature in the cavity 1 is decreased to 33° C., the water temperature of the cooling water in the jacket 2 is controlled to be 1-2.5° C. lower than the temperature in the cavity 1.

Moreover, the water temperature of the cooling water in the jacket 2 is controlled by a setting program, so that the temperature can be gradually and accurately reduced. The reason for the gradual temperature reduction is that if the water temperature of the cooling water in the jacket 2 and the inner cavity temperature of the cavity 1 are not accurately controlled, that is, the temperature difference is too large, it will cause EC to crystallize from the wall and thus the meaning of dynamic crystallization is lost.

Furthermore, the crystal formation in the process of crystallization is initiated by adding a seed crystal at a temperature of 28-29° C., a time for the crystallization is 2-8 h, and the temperature in the cavity 1 during the crystallization is 29-31° C. Specifically, the crystallization process is carried out under a condition of stirring at a stirring speed of 20 r/min, and crystallization is done by stirring with a plurality of rake teeth 5 arranged at intervals at the rotating speed of 20 r/min, so as to obtain small granular crystals.

Moreover, the ethylene carbonate-containing raw material is a direct reaction product and/or an ethylene carbonate material with a content greater than or equal to 80% obtained after preliminary purification of a reaction product. This is because the concentration of EC in the EC reaction product varies while affected by various factors such as differences in synthesis methods, types of catalysts, process conditions, etc. Some of the purity can be higher than 98%, but some of the purity is only 80%, and even some of the purity of the product is lower than 80%. For the reaction product of the purity of lower than 80%, it is necessary to carry out preliminary purification by conventional separation processes such as rectification at reduced pressure, single-stage melting crystallization or membrane separation, and then conduct further separation and purification by employing the method involved in the present invention, so as to obtain an EC product of high purity.

Meanwhile, it should be noted that the amount of the ethylene carbonate-containing raw material entering the cavity 1 is no more than two thirds of the inner cavity volume of the cavity 1, since the crystallization rate and crystallization purity will be affected if it exceeds two thirds of the inner cavity volume of the cavity 1.

The crystallized material flows out from the discharging port 4, and is introduced into a horizontal centrifuge to separate mother liquor from crystals. Industrial-grade small granular ethylene carbonate crystals can be obtained after the mother liquor is discharged, and the non-crystallized mother liquor can be recycled for cycle use. Compared with needle-shaped or flaky crystals obtained during natural crystallization of EC, small granular crystals can be obtained by the dynamic crystallization of the present invention, which meets the industrial-grade requirements. Meanwhile, since no third substance is introduced and the one-time treatment capacity is large, it is convenient to separate the crystallized crystal from the mother liquor, and the method has the characteristics of simple process steps, high product purity, low energy consumption and the like.

The technical solution of the present invention will be further illustrated by specific examples hereafter.

Example 1

1.5 t of an ethylene carbonate-containing raw material was put into the cavity 1 of the rake dryer through the feeding port 3, the temperature at which the ethylene carbonate-containing raw material was put was 45° C., and the water temperature of the cooling water in the jacket 2 was 30° C. High-speed stirring was started so that the rake teeth 5 rotated in the cavity 1 at a rotating speed of 20 r/min. When the inner cavity temperature of the cavity 1 was decreased to nearly 33° C., the water temperature of the cooling water in the jacket 2 was controlled to be 2° C. lower than the temperature in the cavity 1 by a setting program, so as to gradually reduce the temperature until the temperature in the cavity 1 reached 29° C. At this time, 0.1% of a seed crystal was put into the cavity for crystallization for a time of 6 h, and the temperature in the cavity 1 was 29.5° C. during crystallization. After the crystallization, the mother liquor was separated from the crystals by a horizontal centrifuge, so as to obtain small granular ethylene carbonate crystals, and the non-crystallized mother liquor was recycled for cycle use. The purity of the final EC product was 99.94%, the weight of the crystals obtained after crystallization was 985 kg, and the yield was 65.67%. See Table 1.

Example 2

1.8 t of an ethylene carbonate-containing raw material was put into the cavity 1 of the rake dryer through the feeding port 3, the temperature at which the ethylene carbonate-containing raw material was put was 55° C., and the water temperature of the cooling water in the jacket 2 was 30° C. High-speed stirring was started so that the rake teeth 5 rotated in the cavity 1 at a rotating speed of 20 r/min. When the inner cavity temperature of the cavity 1 was decreased to nearly 33° C., the water temperature of the cooling water in the jacket 2 was controlled to be 2° C. lower than the temperature in the cavity 1 by a setting program, so as to gradually reduce the temperature until the temperature in the cavity 1 reached 29° C. At this time, 0.1% of a seed crystal was put into the cavity for crystallization for a time of 6.5 h, and the temperature in the cavity 1 was 29.5° C. during crystallization. After the crystallization, the mother liquor was separated from the crystals by a horizontal centrifuge, so as to obtain small granular ethylene carbonate crystals, and the non-crystallized mother liquor was recycled for cycle use. The purity of the final EC product was 99.85%, the weight of the crystals obtained after crystallization was 1172 kg, and the yield was 65.1%. See Table 1.

Example 3

2.0 t of an ethylene carbonate-containing raw material was put into the cavity 1 of the rake dryer through the feeding port 3, the temperature at which the ethylene carbonate-containing raw material was put was 70° C., and the water temperature of the cooling water in the jacket 2 was 30° C. High-speed stirring was started so that the rake teeth 5 rotated in the cavity 1 at a rotating speed of 20 r/min. When the inner cavity temperature of the cavity 1 was decreased to nearly 33° C., the water temperature of the cooling water in the jacket 2 was controlled to be 2° C. lower than the temperature in the cavity 1 by a setting program, so as to gradually reduce the temperature until the temperature in the cavity 1 reached 29° C. At this time, 0.1% of a seed crystal was put into the cavity for crystallization for a time of 7 h, and the temperature in the cavity 1 was 29.5° C. during crystallization. After the crystallization, the mother liquor was separated from the crystals by a horizontal centrifuge, so as to obtain small granular ethylene carbonate crystals, and the non-crystallized mother liquor was recycled for cycle use. The purity of the final EC product was 99.64%, the weight of the crystals obtained after crystallization was 1269 kg, and the yield was 63.45%. See Table 1.

Comparative Example 1

1.5 t of an ethylene carbonate-containing raw material was put into the cavity 1 of the rake dryer through the feeding port 3, the temperature at which the ethylene carbonate-containing raw material was put was 45° C., and the water temperature of the cooling water in the jacket 2 was 30° C. High-speed stirring was started so that the rake teeth 5 rotated in the cavity 1 at a rotating speed of 10 r/min. When the inner cavity temperature of the cavity 1 was decreased to nearly 33° C., the water temperature of the cooling water in the jacket 2 was controlled to be 2° C. lower than the temperature in the cavity 1 by a setting program, so as to gradually reduce the temperature until the temperature in the cavity 1 reached 29° C. At this time, 0.1% of a seed crystal was put into the cavity for crystallization for a time of 6 h, and the temperature in the cavity 1 was 29.5° C. during crystallization. After the crystallization, the mother liquor was separated from the crystals by a horizontal centrifuge, so as to obtain small granular ethylene carbonate crystals, and the non-crystallized mother liquor was recycled for cycle use. The purity of the final EC product was 99.04%, the weight of the crystals obtained after crystallization was 1004 kg, and the yield was 66.93%. See Table 1.

Comparative Example 2

1.5 t of an ethylene carbonate-containing raw material was put into the cavity 1 of the rake dryer through the feeding port 3, the temperature at which the ethylene carbonate-containing raw material was put was 45° C., and the water temperature of the cooling water in the jacket 2 was 30° C. High-speed stirring was started so that the rake teeth 5 rotated in the cavity 1 at a rotating speed of 30 r/min. When the inner cavity temperature of the cavity 1 was decreased to nearly 33° C., the water temperature of the cooling water in the jacket 2 was controlled to be 2° C. lower than the temperature in the cavity 1 by a setting program, so as to gradually reduce the temperature until the temperature in the cavity 1 reached 29° C. At this time, 0.1% of a seed crystal was put into the cavity for crystallization for a time of 6 h, and the temperature in the cavity 1 was 29.5° C. during crystallization. After the crystallization, the mother liquor was separated from the crystals by a horizontal centrifuge, so as to obtain small granular ethylene carbonate crystals, and the non-crystallized mother liquor was recycled for cycle use. The purity of the final EC product was 99.94%, the weight of the crystals obtained after crystallization was 901 kg, and the yield was 50.07%. See Table 1.

Example 4

1.5 t of an ethylene carbonate-containing raw material was put into the cavity 1 of the rake dryer through the feeding port 3, the temperature at which the ethylene carbonate-containing raw material was put was 45° C., and the water temperature of the cooling water in the jacket 2 was 30° C. High-speed stirring was started so that the rake teeth 5 rotated in the cavity 1 at a rotating speed of 20 r/min. When the inner cavity temperature of the cavity 1 was decreased to nearly 33° C., the water temperature of the cooling water in the jacket 2 was controlled to be 1° C. lower than the temperature in the cavity 1 by a setting program, so as to gradually reduce the temperature until the temperature in the cavity 1 reached 29° C. At this time, 0.1% of a seed crystal was put into the cavity for crystallization for a time of 6 h, and the temperature in the cavity 1 was 29.5° C. during crystallization. After the crystallization, the mother liquor was separated from the crystals by a horizontal centrifuge, so as to obtain small granular ethylene carbonate crystals, and the non-crystallized mother liquor was recycled for cycle use. The purity of the final EC product was 99.93%, the weight of the crystals obtained after crystallization was 985 kg, and the yield was 65.68%. See Table 1.

Example 5

1.5 t of an ethylene carbonate-containing raw material was put into the cavity 1 of the rake dryer through the feeding port 3, the temperature at which the ethylene carbonate-containing raw material was put was 45° C., and the water temperature of the cooling water in the jacket 2 was 30° C. High-speed stirring was started so that the rake teeth 5 rotated in the cavity 1 at a rotating speed of 20 r/min. When the inner cavity temperature of the cavity 1 was decreased to nearly 33° C., the water temperature of the cooling water in the jacket 2 was controlled to be 2.5° C. lower than the temperature in the cavity 1 by a setting program, so as to gradually reduce the temperature until the temperature in the cavity 1 reached 29° C. At this time, 0.1% of a seed crystal was put into the cavity for crystallization for a time of 6 h, and the temperature in the cavity 1 was 29.5° C. during crystallization. After the crystallization, the mother liquor was separated from the crystals by a horizontal centrifuge, so as to obtain small granular ethylene carbonate crystals, and the non-crystallized mother liquor was recycled for cycle use. The purity of the final EC product was 99.92%, the weight of the crystals obtained after crystallization was 986 kg, and the yield was 65.70%. See Table 1.

TABLE 1

| Serial Number | Amount of raw material | Feeding temperature | Temperature difference between water temperature of cooling water and temperature in the kettle | Rotating speed of rake teeth | Crystal shape | Purity of EC crystal | Yield |
| --- | --- | --- | --- | --- | --- | --- | --- |
| Example 1 | 1.5 t | 45° C. | 2° C. | 20 r/min | Granular | 99.94% | 65.67% |
| Example 2 | 1.8 t | 55° C. | 2° C. | 20 r/min | Granular | 99.85% | 65.1% |
| Example 3 | 2.0 t | 70° C. | 2° C. | 20 r/min | Granular | 99.64% | 63.45% |
| Comparative Example 1 | 1.5 t | 45° C. | 2° C. | 10 r/min | Needle-shaped/flaky | 99.04% | 66.93% |
| Comparative Example 2 | 1.5 t | 45° C. | 2° C. | 30 r/min | Granular | 99.94% | 50.07% |
| Example 4 | 1.5 t | 45° C. | 1° C. | 20 r/min | Granular | 99.93% | 65.68% |
| Example 5 | 1.5 t | 45° C. | 2.5° C. | 20 r/min | Granular | 99.92% | 65.70% |

For the method for purifying ethylene carbonate through dynamic crystallization of the present invention, by using the rake dryer as the crystallization device and utilizing a characteristic that the rake dryer can handle a large amount of materials, the temperature difference between the inner cavity temperature of the cavity 1 of the rake dryer and the water temperature of the cooling water in the jacket 2 is controlled to be in the range of 1-2.5° C., so as to realize the dynamic crystallization under the condition of a rotating speed of 15-25 r/min. The reason of controlling the rotating speed of the rake teeth 5 to be 15-25 r/min is that it can be clearly seen from the data in Table 1 that in Comparative Example 1, the rotating speed of the rake teeth 5 is 10 r/min, which is lower than the lower limit of the rotating speed range of 15-25 r/min in the present invention, so only flaky or needle-shaped crystals can be crystallized, resulting in relatively lower crystal purity; in Comparative Example 2, the rotating speed of the rake teeth 5 is 30 r/min, which is higher than the upper limit of the rotating speed range of 15-25 r/min in the present invention, and the yield is low although the purity of the obtained product is not affected.

Meanwhile, in the embodiments of the present invention, an operator should strictly control the timing of adding the seed crystal and the crystallization condition, that is, the temperature at which the seed crystal is added is 28-29° C., and meanwhile, the temperature in the cavity 1 is controlled to be 29-31° C. during crystallization and the time for crystallization is 2-8 h. In the embodiments of the present invention, the maximum handling capacity of the raw material can reach 2.0 t. The purity of the EC crystal can also be up to 99.64% and the yield is 63.45% when 2.0 t of the raw material is processed by utilizing the technical solution of the present invention. It can be seen that the technical solution of the present invention has a large handling capacity and high purification efficiency.

Thirdly, the temperature difference between the water temperature of the cooling water in the jacket 2 and the inner cavity temperature of the cavity 1 should also be strictly controlled in the dynamic crystallization of the present invention, so as to realize gradual temperature reduction. This is because a too large temperature difference will lead to direct crystallization of the EC crystal on the inner wall of the cavity 1, thereby losing the meaning of dynamic crystallization. The expected crystallization effect can be obtained only when gradual temperature reduction is conducted in the temperature difference range that the water temperature of the cooling water in the jacket 2 is 1-2.5° C. lower than the temperature in the kettle in the present invention.

The present invention has been further described by means of specific examples hereinabove, but it should be understood that the specific description here should not be construed as limiting the essence and scope of the present invention, and various modifications made by those of ordinary skills in the art to the aforementioned examples after reading the present specification are all within the claimed scope of the present invention.

The invention claimed is:

1. A method for purifying ethylene carbonate through dynamic crystallization, comprising the following steps: adding an ethylene carbonate-containing raw material into a cavity of a crystallization device through a feeding port of the crystallization device under a condition of stirring for dynamic crystallization, wherein the crystallization device further comprises a jacket attached to an outer wall of the cavity and circumferentially disposed along the outer wall of the cavity, the jacket is provided with cooling water therein, a water temperature of the cooling water in the jacket is controlled to be 1-2.5° C. lower than the temperature in the cavity, and a seed crystal is put to initiate crystallization until a granular ethylene carbonate crystal is generated; and the crystallization device is a rake dryer;

wherein the dynamic crystallization comprises stirring performed by rotating a plurality of stirring parts disposed on an inner wall of the cavity at a rotating speed of 15-25 r/min;

wherein a temperature of the ethylene carbonate-containing raw material entering the cavity is 40-80° C., a water temperature of the cooling water in the jacket is 25-35° C., and when the temperature in the cavity is decreased to 33° C., the water temperature of the cooling water in the jacket is controlled to be 1-2.5° C. lower than the temperature in the cavity;

wherein the crystal formation in the process of crystallization is initiated by adding the seed crystal at a temperature of 28-29° C.;

wherein a time for the crystallization is 2-8 h, and the temperature in the cavity during the crystallization is 29-31° C.

2. The method for purifying ethylene carbonate through dynamic crystallization according to claim 1, wherein the water temperature of the cooling water in the jacket is controlled by a setting program.

3. The method for purifying ethylene carbonate through dynamic crystallization according to claim 1, wherein the ethylene carbonate-containing raw material is a direct reaction product and/or an ethylene carbonate material with a content greater than or equal to 80% obtained after preliminary purification of a reaction product.

4. The method for purifying ethylene carbonate through dynamic crystallization according to claim 1, wherein the amount of the ethylene carbonate-containing raw material entering the cavity is no more than two thirds of an inner cavity volume of the cavity.

5. The method for purifying ethylene carbonate through dynamic crystallization according to claim 1, wherein the crystallized material is introduced into a centrifuge to separate mother liquor from a crystal.

* * * * *